United States Patent
Do Choi et al.

(10) Patent No.: US 8,637,669 B2
(45) Date of Patent: Jan. 28, 2014

(54) PRODUCTION METHOD FOR ADEFOVIR DIPIVOXIL

(75) Inventors: Kwang Do Choi, Anyang-si (KR); Yong Tack Lee, Seoul (KR); Myeong Sik Yoon, Yongin-si (KR); Hye Suk Hong, Seongnam-si (KR); Il Hwan Cho, Seoul (KR); Si Beum Lee, Yongin-si (KR); Seong Cheol Bang, Nonsan-si (KR); Da Won Oh, Seoul (KR); Min Kyoung Lee, Yongin-si (KR)

(73) Assignee: CJ Cheiljedang Corporation, Seoul (KR)

( * ) Notice: Subject to any disclaimer, the term of this patent is extended or adjusted under 35 U.S.C. 154(b) by 235 days.

(21) Appl. No.: 13/119,538

(22) PCT Filed: Sep. 17, 2009

(86) PCT No.: PCT/KR2009/005305
§ 371 (c)(1),
(2), (4) Date: May 4, 2011

(87) PCT Pub. No.: WO2010/032974
PCT Pub. Date: Mar. 25, 2010

(65) Prior Publication Data
US 2011/0207930 A1  Aug. 25, 2011

(30) Foreign Application Priority Data

Sep. 18, 2008  (KR) .................. 10-2008-0091390
Jan. 8, 2009  (KR) .................. 10-2009-0001394

(51) Int. Cl.
*C07F 9/6561* (2006.01)
*C07D 473/34* (2006.01)
*C07F 9/28* (2006.01)
*C07F 9/40* (2006.01)
*A61K 31/675* (2006.01)
*C07F 9/00* (2006.01)

(52) U.S. Cl.
USPC ........................................ 544/234

(58) Field of Classification Search
USPC ........................................ 544/244
See application file for complete search history.

(56) References Cited

U.S. PATENT DOCUMENTS 5,663,159 A  9/1997 Starrett, Jr. et al. .......... 514/181
2002/0045599 A1  4/2002 Arimilli et al. ............... 514/81

FOREIGN PATENT DOCUMENTS

| CN | 1935818 A |   | 3/2007 |
| CN | 101357930 A | * | 2/2009 |
| KR | 10-0700087 B1 |   | 3/2007 |
| WO | WO 99/04774 |   | 2/1999 |
| WO | WO 2007/013085 |   | 2/2007 |

OTHER PUBLICATIONS

IUPAC, "reversed-phase chromatography" http://goldbook.iupac.org/R05376.html downloaded from the internet Feb. 20, 2012.*
Molnár Clinical Chemistry 22 (9): 1497-1502 (1976).*
Mehta, "Principle of Reversed-Phase Chromatography HPLC/UPLC" http://pharmaxchange.info/press/2012/12/principle-of-reversed-phase-chromatography-hplcuplc-with-animation/ downloaded from the internet Feb. 20, 2012.*
Tosoh, "Principles of Reversed Phase Chromatography" http://www.separations.eu.tosohbioscience.com/ServiceSupport/TechSupport/ResourceCenter/PrinciplesofChromatography/ReversedPhase/ downloaded from the internet Feb. 20, 2012.*
"Reversed Phase Chromatography (RPC)" http://mach7.bluehill.com/proteinc/tutorial/rpc.html downloaded from the internet Feb. 20, 2012.*
Bi et al., "Determination of adefovir in human plasma by liquid chromatography/tandem mass spectrometry: application to a pharmacokinetic study," *Rapid Communications in Mass Spectrometry* 19:2911-2917, 2005.
Extended European Search Report, for European Application No. 09814790.3, dated Sep. 20, 2011, 6 pages.
Liu et al., "Synthesis of adefovir dipivoxil," Chemical Abstracts Database, Accession No. 2006:867505, 2005, 2 pages.
Shi et al., "TLC Determination of Related Substances in Adefovir Dipivoxil," Chemical Abstracts Database, Accession No. 2005:500302, 2004, 1 page.
Starrett, Jr. et al., "Synthesis, Oral Bioavailability Determination, and in Vitro Evaluation of Prodrugs of the Antiviral Agent 9-[2-(Phosphonomethoxy)ethyl]adenine (PMEA)," *Journal of Medicinal Chemistry* 37:1857-1864, 1994.

* cited by examiner

*Primary Examiner* — Kortney L Klinkel
*Assistant Examiner* — John Mauro
(74) *Attorney, Agent, or Firm* — Seed IP Law Group PLLC

(57) ABSTRACT

The present invention relates to an improved method of preparing adefovir dipivoxil of Formula 1. The method of the present invention is characterized by using dimethylsulfoxide as a reaction solvent, and comprises a process of preparing adefovir dipivoxil of Formula 1 by allowing adefovir of Formula 2 to react with chloromethylpivalate at a reaction temperature of 30 to 50° C. under the presence of dimethylsulfoxide and triethylamine solvents.

[Formula 1]

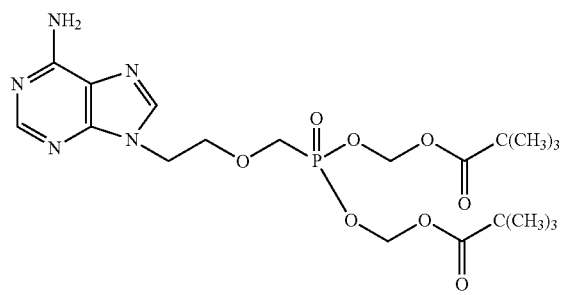

-continued

[Formula 2]

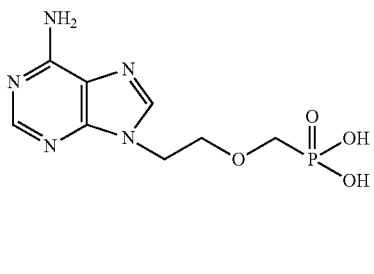

7 Claims, 4 Drawing Sheets

PRODUCTION METHOD FOR ADEFOVIR DIPIVOXIL

TECHNICAL FIELD

The present invention relates to an improved method of preparing adefovir dipivoxil, 9-[2-[[bis{(pivaloyloxy)-methoxy}phosphinyl]methoxy]ethyl]adenine, useful as an antiviral agent which has been disclosed in U.S. Pat. No. 5,663,159. In particular, the present invention relates to an improved method of preparing 9-[2-[[bis{(pivaloyloxy)-methoxy}phosphinyl]methoxy]ethyl]adenine ("adefovir dipivoxil") of Formula 1 by using 9-[2-(phosphonomethoxy)ethyl]adenine ("adefovir") of Formula 2 as a starting material.

[Formula 1]

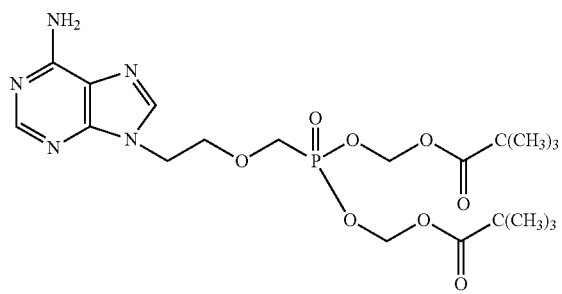

[Formula 2]

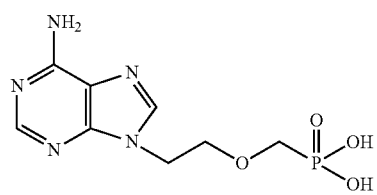

BACKGROUND ART

Adefovir dipivoxil, which is a useful antiviral drug, is a nucleotide reverse transcriptase inhibitor, which exhibits a marked in vivo antiviral activity against especially both HIV and Hepatitis type B virus (HBV). The adefovir dipivoxil has been sold on the market under the trademark "Hepsera."

Adefovir dipivoxil can be prepared, for example, according to a method as described in U.S. Pat. No. 5,663,159. The document discloses the method for preparation of adefovir dipivoxil of Formula 1 comprising reacting adefovir of Formula 2 as a starting material with chloromethylpivalate at a temperature of 22° C. under the presence of dimethylformamide (DMF) and N,N'-dicyclohexyl-4-morpholine-carboxamidine to give a yield of 32% of adefovir dipivoxil.

[Reaction Scheme 1]

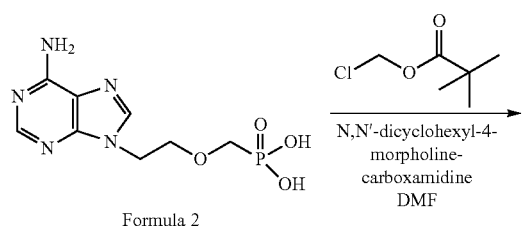

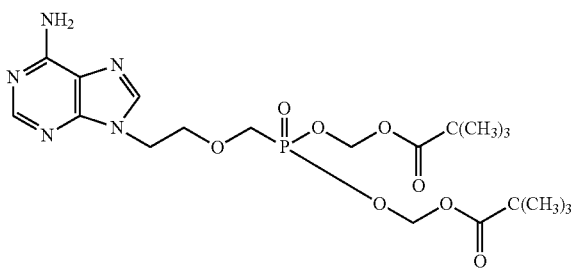

Formula 1

However, the above method has a problem in that large quantities of byproducts are generated during the synthetic reaction, which results in a low yield of adefovir dipivoxil.

In order to solve the problem, Korean Patent No. 0700087 discloses a method of synthesizing adefovir dipivoxil of Formula 1 by allowing adefovir of Formula 2 as a starting material to react with chloromethylpivalate under the presence of 1-methyl-2-pyrrolidone (NMP) and triethylamine (TEA), which is represented by the following Reaction Scheme 2.

[Reaction Scheme 2]

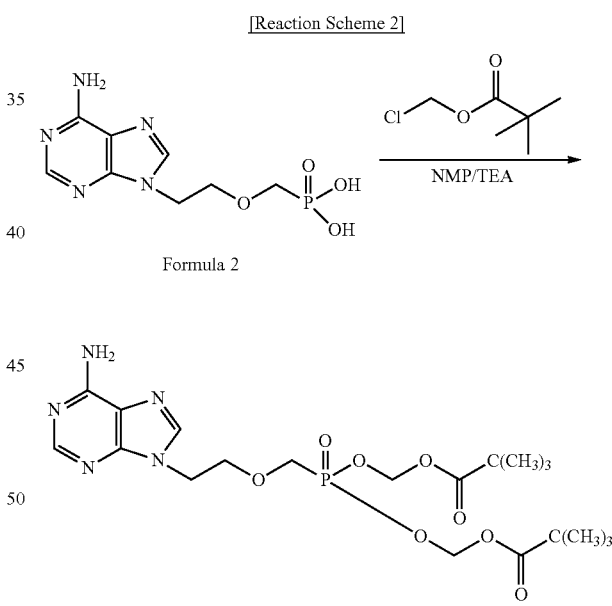

Formula 1

The above method shows the improvement in a yield of adefovir dipivoxil by approximately 55%, but there are still problems in that since its reaction temperature should be increased to 60° C. or higher, related compounds (impurities) are thus generated in abundance, and the amount of 1-methyl-2-pyrrolidone used in the reaction and byproducts of Formula 3 generated during the reaction accounts for about 15% or higher of final products, which makes it difficult to purify adefovir dipivoxil.

[Formula 3]

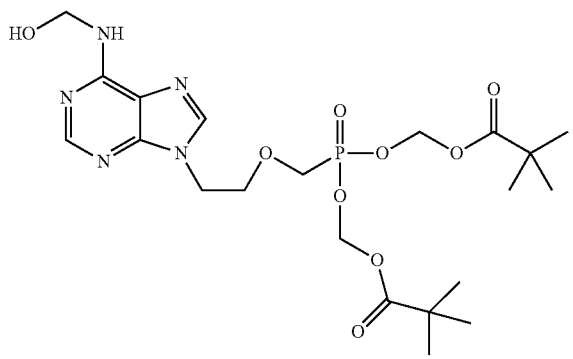

DISCLOSURE

Technical Problem

An object of the present invention is to provide a novel method of preparing adefovir dipivoxil of Formula 1 which shows high reaction yields of adefovir dipivoxil with low production of byproducts and is carried out under improved reaction conditions. The present invention can achieve the object by using dimethylsulfoxide as a reaction solvent, thereby providing an improved method of preparing adefovir dipivoxil of Formula 1.

Technical Solution

According to the present invention, there is provided an improved method of preparing 9-[2-[[bis{(pivaloyloxy)-methoxy}phosphinyl]methoxy]ethyl]adenine ("adefovir dipivoxil") of Formula 1 by using 9-[2-(phosphonomethoxy) ethyl]adenine ("adefovir") of Formula 2.

The method according to the present invention is characterized by using dimethylsulfoxide as a reaction solvent instead of 1-methyl-3-pyrrolidone, and comprises reacting adefovir of Formula 2 with chloromethylpivalate at a temperature of 30 to 50° C. for 3 to 7 hours under the presence of dimethylsulfoxide and triethylamine solvents to give adefovir dipivoxil of Formula 1.

Further, adefovir dipivoxil prepared according to the method of the present invention is characterized by containing 15% or less of byproducts of Formula 3.

Advantageous Effects

According to a method of the present invention, since 15% or less of byproducts of Formula 3 is contained in final products, it can prepare a high yield of adefovir dipivoxil with good quality. Further, the reaction in the method is carried out faster even at lower reaction temperature than conventional methods (using NMP), thereby decreasing production of related compounds.

In addition, since dimethylsulfoxide that is a reaction solvent is easily removed and its reaction is carried out at moderate reaction temperature, the method of the present invention provides an additional advantage of improved reaction conditions.

MODE FOR INVENTION

Figure 1:
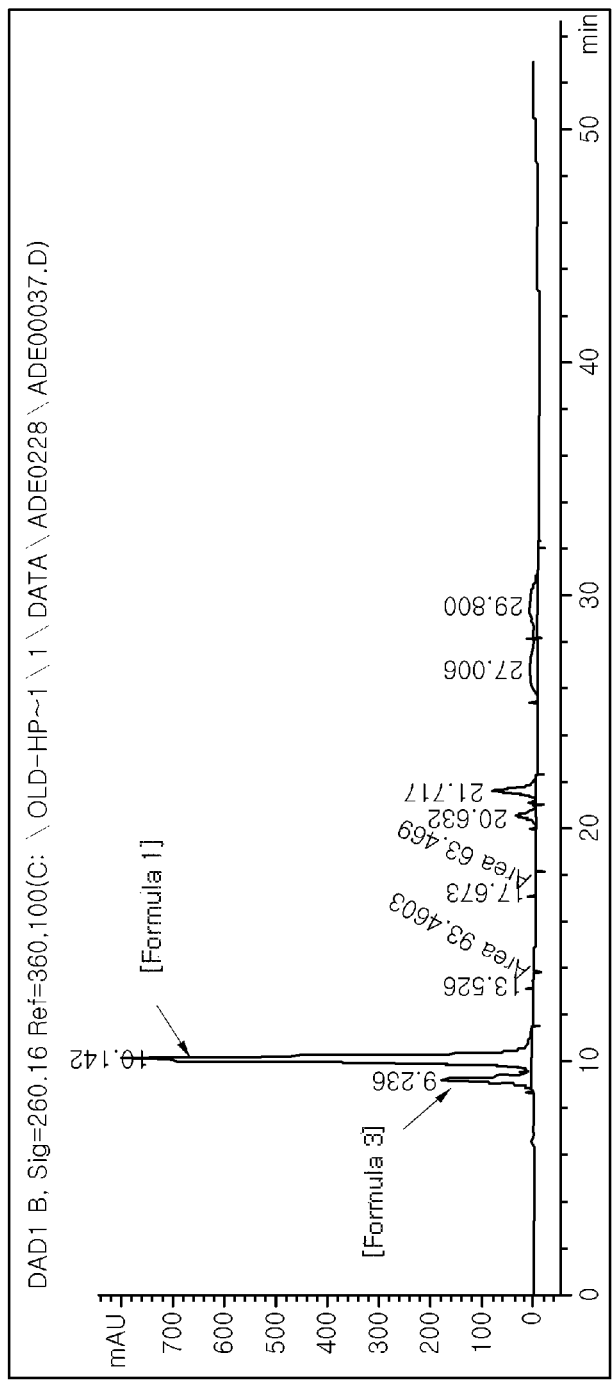
FIG. 1 is a HPLC spectrum of analyzing a synthetic product obtained in Example 1.

Hereinafter, a preparation method of the present invention will be described in detail.

In accordance with a method of the present invention, the reaction of synthesizing adefovir dipivoxil of Formula 1 by using adefovir of Formula 2 as a starting material is illustrated by the following Reaction Scheme 3.

[Reaction Scheme 3]

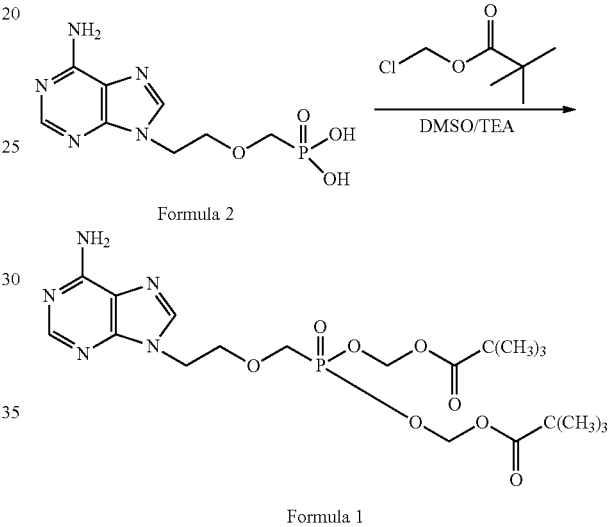

Adefovir of Formula 2 is added to a mixture of dimethylsulfoxide and triethylamine, and then, chloromethylpivalate is added thereto drop by drop. Then, the resulting mixture is stirred for 3 to 7 hours while maintaining a reaction temperature of 30 to 50° C., to thereby obtain adefovir dipivoxil of Formula 1.

The method of the present invention may further comprise the following purification process for removing byproducts included in the prepared adefovir dipivoxil of Formula 1.

The purification process comprises the steps of dissolving the prepared adefovir dipivoxil of Formula 1 in water or a water-containing mixed solvent; purifying the adefovir dipivoxil solution through a reverse-phase column; and adding a base to the purified adefovir dipivoxil solution, followed by extracting it with an organic solvent.

Specifically, according to the purification process described above, water or a water-containing mixed solvent is added to the organic solvent layer in which impure adefovir dipivoxil containing byproducts generated during the synthetic reaction is dissolved, an acid is added thereto, and then, adefovir dipivoxil is extracted into an aqueous layer. The water-containing mixed solvent used in the present invention refers to an organic solvent in which at least 20% by weight of water is dissolved. An example of suitable organic solvents may include $C_1$~$C_4$ alcohol, acetone, acetonitrile, tetrahydrofuran, dioxane and the like, but are not limited thereto.

Adefovir dipivoxil containing byproducts in the organic solvent reacts with the acid to give its salts or complexes, which can be then dissolved in water or the water-containing mixed solvent. The term "salt" or "complex" of adefovir dipivoxil as used herein refers to a compound prepared by mixing adefovir dipivoxil with an inorganic acid or an organic acid.

The acid used in the present invention can be inorganic acids or organic acids, and examples thereof may include hydrochloric acid, sulfuric acid, nitric acid and methanesulfonic acid in consideration of the formation of salts or complexes of adefovir dipivoxil.

In addition, pH of the extracted aqueous solution is in a range of 0.1 to 5.0, preferably 1.0 to 3.0.

The separated aqueous solution is allowed to pass through a reverse-phase column, eluted, and then, collected as an eluate. If necessary, an aqueous solution (mobile phase) having a pH range of 0.1 to 5.0, preferably 1.0 to 3.5 may be further allowed to pass through the reverse-phase column, eluted and collected.

Packaging materials (stationary phase) used in the reverse-phase column include polymers that are immiscible with water such as $C_1\sim C_{18}$ alkyl and $HP_2O$, and it is preferable to use $C_{18}$ octadecyl.

An organic solvent is added to the collected aqueous solution, followed by adding a base thereto to thereby adjust pH of the aqueous solution to a range of 2.5 to 10. Thereafter, the organic solvent is removed therefrom.

Exemplary organic solvents used here may include dichloromethane, isopropylacetate, toluene, ethylacetate and the like, and it is preferable to use dichloromethane or isopropylacetate.

Further, the base used here may be inorganic bases or organic bases. When considering the generation of related compounds, pH. of the aqueous solution to which the base added is preferably in a range of 2.5 to 6.5.

Thereafter, the collected organic solvent is removed to thereby obtain purified amorphous adefovir dipivoxil solids with high purity.

Here, the organic solvent can be removed by concentrating the aqueous solution under reduced pressure, and during the concentration, an inner temperature of 30° C. to 90° C. is preferable.

Besides the concentration under reduced pressure, the organic solvent can be removed by adding the concentrated solution of adefovir dipivoxil represented by Formula 1 to $C_5\sim C_{12}$ hydrocarbons, such as n-pentane, n-hexane, n-heptane, cyclohexane and the like, drop by drop, thereby forming amorphous solids, followed by filtration.

Adefovir dipivoxil purified according to the method of the present invention has a purity of 95% or higher, preferably 99% or higher.

Hereinafter, examples will be presented in order to help understand the present invention. However, the following examples are provided for the purpose of easily understanding the present invention and are not construed as being limited to the scope of the present invention.

EXAMPLE 1

Preparation Method of Adefovir Dipivoxil, 9-[2-[[bis{(pivaloyloxy)-methoxy}phosphinyl]methoxy]ethyl]adenine, Represented by Formula 1

100 g of 9-[2-(Phosphonomethoxy)ethyl]adenine ("adefovir") and 400 g of dimethylsulfoxide were inputted into a reactor. Thereafter, 140 mg of triethylamine and 250 g of chloromethylpivalate were subsequently added thereto, and then, the mixture was heated to a reaction temperature of 40° C. and stirred for 5 hours.

After the mixture was cooled down to a temperature of 10 to 20° C., 500 ml of dichloromethane and 1000 ml of distilled water were added thereto, followed by stirring for 5 minutes. As a result, an organic layer was separated.

The obtained synthetic product was analyzed through HPLC. HPLC analysis was carried out by using an Alltech Mixed Mode Exchange™ C8 (7 u, 100 Å) as a column and a UV spectrophotometer (observed at a wavelength of 260 nm) was used as a detector, under conditions of a flow rate of 1.2 ml/min and a column temperature of room temperature. A mixture of phosphate buffer (pH 6.0) and acetonitrile at a ratio of 70:30 was used as a mobile phase A, a mixture of phosphate buffer (pH 6.0) and acetonitrile at a ratio of 50:50 was used as a mobile phase B, and a mixture of phosphate buffer (pH 3.0) and acetonitrile at a ratio of 20:30 was used as a diluting agent.

In a column analysis of mobile phases A and B, a change in inflow amount was as follows.

| Time (min) | Mobile phase A (%) | Mobile phase B (%) |
| --- | --- | --- |
| 0 to 19 | 100→0 | 0→100 |
| 19 to 36 | 0 | 100 |
| 36 to 46 | 0→100 | 100→0 |

The results of analyzing the synthetic product obtained in Example 1 with HPLC under the conditions described above are shown in FIG. 1 (in case of adefovir dipivoxil of Formula 1, RetTime (min): 10.142, Width (min): 0.27, Area (mAU*s): 1.45561e4, Height (mAU): 810.53, and Area (%): 61.55; in case of byproduct of Formula 3, RetTime (min): 9.236, Width (min): 0.23, Area (mAU*s): 2927.66, Height (mAU): 184.96, and Area (%): 12.38).

EXAMPLE 2

Preparation Method of Adefovir Dipivoxil, 9-[2-[[bis{(pivaloyloxy)-methoxy}phosphinyl]methoxy]ethyl]adenine, Represented by Formula 1

100 g of 9-[2-(Phosphonomethoxy)ethyl]adenine ("adefovir") and 400 g of dimethylsulfoxide were inputted into a reactor. Thereafter, 140 mg of triethylamine and 250 g of chloromethylpivalate were subsequently added thereto, and then, the mixture was heated to a reaction temperature of 43° C. and stirred for 4 hours.

After the mixture was cooled down to a temperature of 10 to 20° C., 500 ml of dichloromethane and 1000 ml of distilled water were added thereto, followed by stirring for 5 minutes. As a result, an organic layer was separated.

Figure 2:
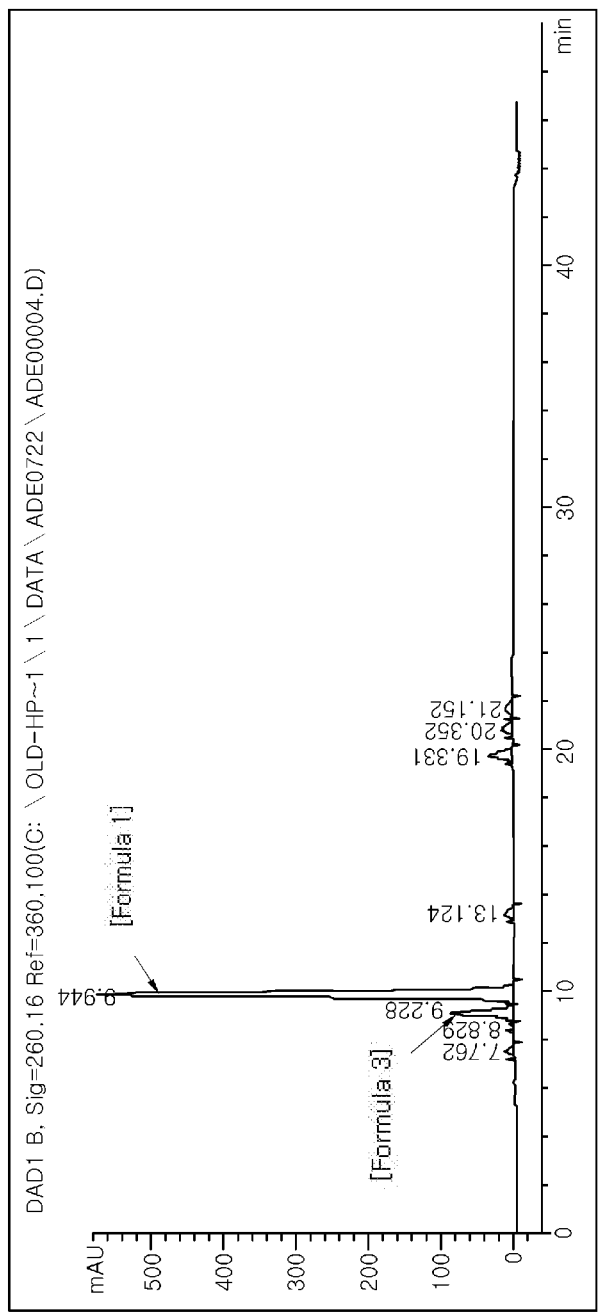
FIG. 2 is a HPLC spectrum of analyzing a synthetic product obtained in Example 2.

The obtained synthetic product was analyzed through HPLC. HPLC analysis was carried out under the same conditions as described in Example 1. The results of analyzing the synthetic product obtained in Example 2 with HPLC are shown in FIG. 2 (in case of adefovir dipivoxil of Formula 1, RetTime (min): 9.944, Width (min): 0.23, Area (mAU*s): 8248.92, Height (mAU): 549.31, and Area (%): 75.68; in case of byproduct of Formula 3, RetTime (min): 9.228, Width (min): 0.22, Area (mAU*s): 1208.14, Height (mAU): 85.30, and Area (%): 11.08).

EXAMPLE 3

Preparation Method of Adefovir Dipivoxil, 9-[2-[[bis{(pivaloyloxy)-methoxy}phosphinyl]methoxy]ethyl]adenine, Represented by Formula 1

100 g of 9-[2-(Phosphonomethoxy)ethyl]adenine ("adefovir") and 400 g of dimethylsulfoxide were inputted into a reactor. Thereafter, 140 mg of triethylamine and 250 g of chloromethylpivalate were subsequently added thereto, and then, the mixture was heated to a reaction temperature of 38° C. and stirred for 6 hours.

After the mixture was cooled down to a temperature of 10 to 20° C., 500 ml of dichloromethane and 1000 ml of distilled water were added thereto, followed by stirring for 5 minutes. As a result, an organic layer was separated.

Figure 3:
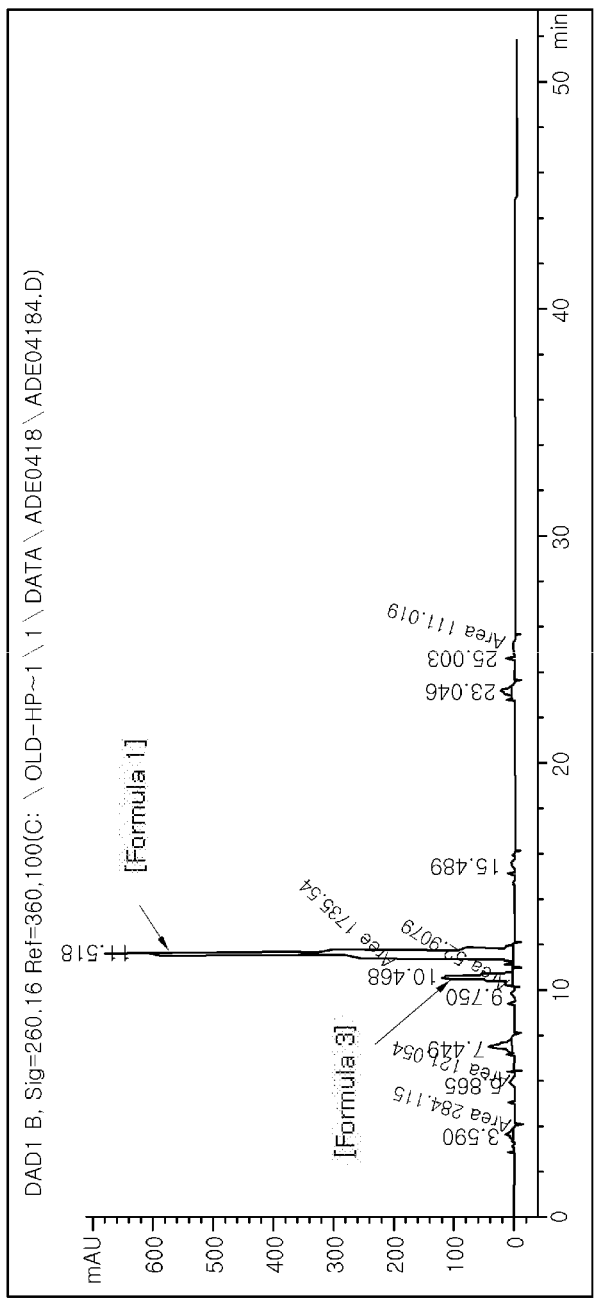
FIG. 3 is a HPLC spectrum of analyzing a synthetic product obtained in Example 3.

The obtained synthetic product was analyzed through HPLC. HPLC analysis was carried out under the same conditions as described in Example 1. The results of analyzing the synthetic product obtained in Example 3 with HPLC are shown in FIG. 3 (in case of adefovir dipivoxil of Formula 1, RetTime (min): 11.518, Width (min): 0.22, Area (mAU*s): 9995.02, Height (mAU): 682.72, and Area (%): 73.83; in case of byproduct of Formula 3, RetTime (min): 10.466, Width (min): 0.24, Area (mAU*s): 1735.54, Height (mAU): 122.53, and Area (%): 12.82).

EXAMPLE 4

Preparation Method of Adefovir Dipivoxil, 9-[2-[[bis{(pivaloyloxy)-methoxy}phosphinyl]methoxy]ethyl]adenine, Represented by Formula 1

100 g of 9-[2-(Phosphonomethoxy)ethyl]adenine ("adefovir") and 400 g of dimethylsulfoxide were inputted into a reactor. Thereafter, 150 mg of triethylamine and 300 g of chloromethylpivalate were subsequently added thereto, and then, the mixture was heated to a reaction temperature of 40° C. and stirred for 5 hours.

After the mixture was cooled down to a temperature of 10 to 20° C., 500 ml of dichloromethane and 1000 ml of distilled water were added thereto, followed by stirring for 5 minutes. As a result, an organic layer was separated.

Figure 4:
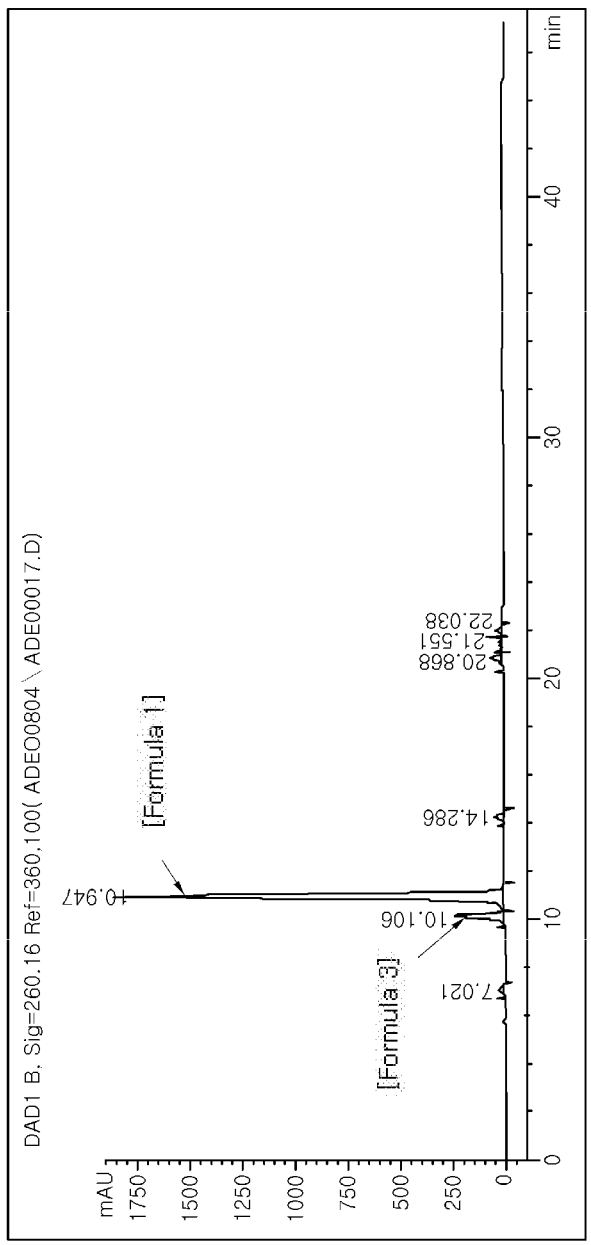
FIG. 4 is a HPLC spectrum of analyzing a synthetic product obtained in Example 4.

The obtained synthetic product was analyzed through HPLC. HPLC analysis was carried out under the same conditions as described in Example 1. The results of analyzing the synthetic product obtained in Example 4 with HPLC are shown in FIG. 4 (in case of adefovir dipivoxil of Formula 1, RetTime (min): 10.947, Width (min): 0.20, Area (mAU*s): 2.40482e4, Height (mAU): 1845.69, and Area (%): 82.04; in case of byproduct of Formula 3, RetTime (min): 10.106, Width (min): 0.18, Area (mAU*s): 2710.89, Height (mAU): 232.66, and Area (%): 9.25).

EXAMPLE 5

Purification Method of Adefovir Dipivoxil, 9-[2-[[bis{(pivaloyloxy)-methoxy}phosphinyl]methoxy]ethyl]adenine, Represented by Formula 1

3000 ml of distilled water was added to the organic layer obtained in Example 1. After pH of the distilled water was adjusted to 1.8 by adding 1 N hydrochloric acid, it was stirred at a temperature of 20 to 25° C. for 10 minutes. The stirring was stopped, and then, an aqueous layer was separated. The separated aqueous layer was allowed to pass through a $C_{18}$ reverse-phase column (size: 40×15 cm, packing substance: KP-$C_{18}$-HSTM 35~70 um, 90 Å C18-bonded silica, manufacturer: Biotage).

The aqueous solution passing through the $C_{18}$ reverse-phase column was collected, and the $C_{18}$ reverse-phase column was sequentially washed with methanol and pH 2.0 hydrochloric acid solution.

After the obtained aqueous solution was allowed to pass through the $C_{18}$ reverse-phase column and eluted therefrom, the re-collected aqueous solution was mixed with 500 ml of dichloromethane. 5% sodium bicarbonate was added to the reaction mixture drop by drop while stirred to adjust pH of the collected aqueous solution to a range of 5.5 to 5.6.

After the stirring was stopped, dichloromethane was separated, followed by dehydrating with sodium sulfate and filtering.

The filtered dichloromethane was concentrated under reduced pressure. 500 ml of n-hexane was added to the formed solid, stirred, and then, filtered, to thereby obtain amorphous high purity adefovir dipivoxil represented by Formula 1 (yield: 43 g (23.9%), purity: 99.8%).

EXAMPLE 6

Purification Method of Adefovir Dipivoxil, 9-[2-[[bis{(pivaloyloxy)-methoxy}phosphinyl]methoxy]ethyl]adenine, Represented by Formula 1

3000 ml of distilled water was added to the organic layer obtained in Example 2. After pH of the distilled water was adjusted to 2.2 by adding methanesulfonic acid, it was stirred at a temperature of 20 to 25° C. for 10 minutes. The stirring was stopped, and then, an aqueous layer was separated. The separated aqueous layer was allowed to pass through a $C_{18}$ reverse-phase column (size: 40×15 cm, packing substance: KP-$C_{18}$-HSTM 35~70 um, 90 Å C18-bonded silica, manufacturer: Biotage).

The aqueous solution passing through the $C_{18}$ reverse-phase column was collected, and the $C_{18}$ reverse-phase column was sequentially washed with methanol and pH 2.3 hydrochloric acid solution.

After the obtained aqueous solution was allowed to pass through the $C_{18}$ reverse-phase column and eluted therefrom, the re-collected aqueous solution was mixed with 500 ml of dichloromethane. 5% sodium bicarbonate was added to the reaction mixture drop by drop while stirred to adjust pH of the collected aqueous solution to a range of 3.2 to 3.3.

After the stirring was stopped, dichloromethane was separated, followed by dehydrating with sodium sulfate and filtering.

The filtered dichloromethane was concentrated under reduced pressure, to thereby obtain amorphous high purity adefovir dipivoxil represented by Formula 1 (yield: 45 g (25.1%), purity: 99.7%).

EXAMPLE 7

Purification Method of Adefovir Dipivoxil, 9-[2-[[bis{(pivaloyloxy)-methoxy}phosphinyl]methoxy]ethyl]adenine, Represented by Formula 1

3000 ml of distilled water was added to the organic layer obtained in Example 3. After pH of the distilled water was adjusted to 2.2 by adding methanesulfonic acid, it was stirred at a temperature of 20 to 25° C. for 10 minutes. The stirring was stopped, and then, an aqueous layer was separated. The separated aqueous layer was allowed to pass through a $C_{18}$ reverse-phase column (size: 40×15 cm, packing substance: KP-$C_{18}$-HSTM 35~70 um, 90 Å C18-bonded silica, manufacturer: Biotage).

The aqueous solution passing through the $C_{18}$ reverse-phase column was collected, and the $C_{18}$ reverse-phase column was sequentially washed with methanol and pH 2.3 hydrochloric acid solution.

After the obtained aqueous solution was allowed to pass through the $C_{18}$ reverse-phase column and eluted therefrom, the re-collected aqueous solution was mixed with 500 ml of dichloromethane. 5% sodium bicarbonate was added to the reaction mixture drop by drop while stirred to adjust pH of the collected aqueous solution to a range of 3.1 to 3.2.

After the stirring was stopped, dichloromethane was separated, followed by dehydrating with sodium sulfate and filtering.

The filtered dichloromethane was concentrated under reduced pressure, to thereby obtain amorphous high purity adefovir dipivoxil represented by Formula 1 (yield: 45 g (25.1%), purity: 99.7%).

The invention claimed is:

1. A method of preparing adefovir dipivoxil of Formula 1, comprising the step of reacting adefovir of Formula 2 with chloromethylpivalate under the presence of dimethylsulfoxide and triethylamine solvents:

[Formula 1]

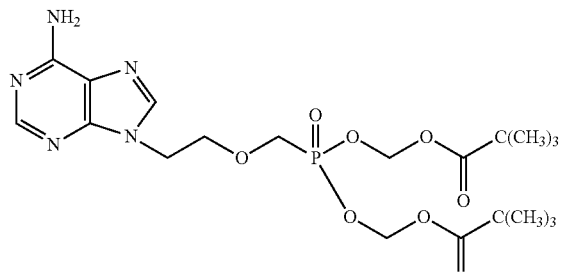

[Formula 2]

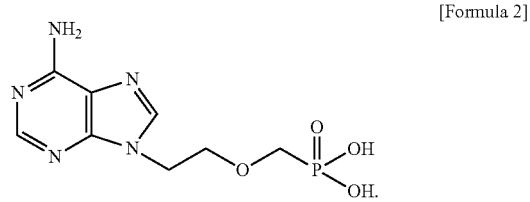

2. The method of claim 1, wherein the prepared adefovir dipivoxil of Formula 1 contains 15% or less of byproducts of Formula 3:

[Formula 3]

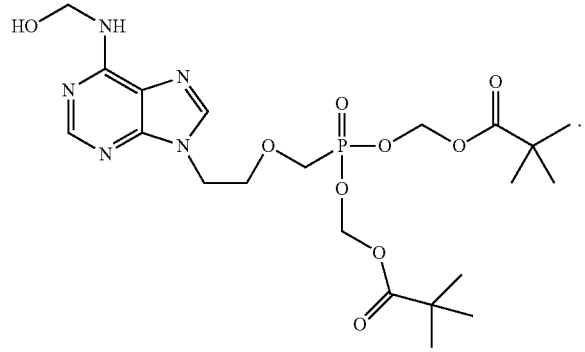

3. The method of claim 1, wherein the reaction is carried out at a temperature of 30 to 50° C.

4. The method of any one of claims 1 to 3, wherein the reaction is carried out for 3 to 7 hours.

5. The method of any one of claims 1 to 3, further comprising the step of purifying the prepared adefovir dipivoxil of Formula 1.

6. The method of claim 5, wherein the purification step comprises the steps of dissolving the prepared adefovir dipivoxil of Formula 1 in water or a water-containing mixed solvent; purifying the adefovir dipivoxil solution through a reverse-phase column of which a stationary phase is hydrophobic; adding an organic solvent to the purified adefovir dipivoxil solution; and adding a base to the organic solvent-added solution.

7. The method of claim 6, wherein the water-containing mixed solvent is a solvent in which water is dissolved in one or more solvents selected from the group consisting of C1 to C4 alcohol, acetone, acetonitrile, tetrahydrofuran, and dioxane in a concentration of 20 wt % or higher.

* * * * *